United States Patent [19]
Zang

[11] Patent Number: 5,336,225
[45] Date of Patent: Aug. 9, 1994

[54] BONE FASTENING DEVICE
[75] Inventor: Kerry Zang, Paradise Valley, Ariz.
[73] Assignee: Orthopaedic Biosystems, Ltd., Scottsdale, Ariz. ; a part interest
[21] Appl. No.: 946,815
[22] Filed: Sep. 17, 1992

Related U.S. Application Data

[63] Continuation of Ser. No. 705,374, May 24, 1991, abandoned.

[51] Int. Cl.⁵ .................................................. A61F 5/04
[52] U.S. Cl. ........................................ 606/73; 606/60; 411/398
[58] Field of Search ...................... 128/69; 606/60, 61, 606/62, 64, 68–73, 53; 411/378, 398, 402, 388, 389, 396, 397, 401, 411

[56] References Cited

U.S. PATENT DOCUMENTS

| | | | |
|---|---|---|---|
| 274,743 | 3/1883 | Shane | 411/398 |
| 2,242,003 | 5/1941 | Lorenzo | 606/73 |
| 2,489,870 | 11/1949 | Dzus | 128/92 |
| 3,779,240 | 12/1973 | Kondo | 606/69 |
| 4,041,939 | 8/1977 | Hall | 128/69 |
| 4,367,970 | 1/1983 | Franz | 411/378 |
| 4,468,200 | 8/1984 | Münch | 606/73 |
| 4,569,338 | 2/1986 | Edwards | 128/69 |
| 4,711,232 | 12/1987 | Fischer et al. | 128/92 |
| 4,711,234 | 12/1987 | Vives et al. | 128/92 |
| 4,827,917 | 5/1989 | Brumfield | 128/92 |

Primary Examiner—Danton D. DeMille
Assistant Examiner—David Kenealy
Attorney, Agent, or Firm—David G. Rosenbaum

[57] ABSTRACT

A surgical bone screw having a head which has asymmetrical radii relative to the central axis of the screw. The cross-section of the head is configured as a lobular shape having a constant radii along one hemisphere of the head, and smaller radii along the opposing hemisphere of the head, with the smallest radius existing approximately perpendicular to the midline of the head member. The asymmetry of the head minimizes surface area of the screw protruding above the bone surface.

14 Claims, 1 Drawing Sheet

BONE FASTENING DEVICE

This is a continuation of copending application Ser. No. 07/705,374 filed on May 24, 1991 now abandoned.

BACKGROUND OF THE INVENTION

The present invention relates generally to devices for fastening fractured bones. More particularly, this invention relates to an improved bone screw which facilitates minimizing protrusion of the head from the surface of the bone into which the screw is affixed.

It is standard orthopedic procedure to reduce a fracture and secure the reduction with a fastening device inserted into the bone to join the fractured bones. Bone screws are customarily used to reduce the fracture and maintain the fractured bone pieces in physiologically normal alignment during the subsequent healing process. A number of bone fixation devices are known in the art.

Specifically, U.S. Pat. No. 2,489,870 to Dzus discloses a bone fastening device consisting of a lag screw, i.e., a screw having a threaded end portion and a smooth shaft portion, a stud which screwably engages the lag screw and a retaining clip, which is engaged by the stud and tensioned against a bone by action between the lag screw and the stud. The Dzus fastening device is especially useful in correcting spreading of adjacent bones, such as spread mortise of the ankle bones.

U.S. Pat. No. 4,041,939 to Hall, discloses a surgical implant spinal screw which is characterized by a head member having lateral bores for receiving an alignment pin to maintain intervertebral alignment for correction of scoliosis.

U.S. Pat. No. 4,711,232 to Fischer et al discloses a bone fastener consisting of a surgical screw and sleeve. The surgical screw has a head portion having a generally radial symmetry relative to the central axis of the screw. The surgical bone screw of the Fischer et al patent is representative of bone screws widely employed in reducing fracture of small bones, such as the metacarpals and metatarsals.

U.S. Pat. No. 4,569,338 issued to Edwards discloses a sacral fixation screw which has a head member having a laterally oriented slot passing entirely through the lateral aspects of the head. The slot permits engagement of a sacral rod and hook to facilitate longitudinal adjustment of the sacroiliac joint.

Finally, U.S. Pat. No. 4,827,917 to Brumfield discloses a femoral fracture device consisting of a screw and an intramedullary rod. The screw is a lag screw having a head member which has generally radial symmetry relative to a central axis of the screw.

It has been found that the surgical screws typified by the Brumfield and Dzus patents, i.e., those having screw heads with radial symmetry relative to the central axis of the screw, are not ideally well-suited to use in reducing fractures of the bones in the hands or feet. Fractures occurring in the hand or foot, typically involving the metacarpal and metatarsal bones, respectively, present difficulty in reduction due to the narrow diameter of the bone. Moreover, because these bones have closely associated tendons, muscles and ligaments, the protrusion of the screw head above the surface of the bone often causes inflammation of the associated tissues. The resulting inflammation presents a debilitating environment which is not conducive to healing of the bone.

Accordingly, there is a need for a modified surgical screw having modified head configured to minimize protrusion above the surface of the bone.

SUMMARY OF THE INVENTION

It is a broad object of the invention, therefore, to provide a surgical bone screw which has a head configured to minimize the surface area protruding from the surface of the bone. The smaller protruding surface area will reduce the incidence of inflammation of the surrounding tissue, and facilitate a healthier environment for regeneration and healing of the bone.

The inventive surgical bone screw is characterized by a head having asymmetrical radii relative to the central axis of the screw. Specifically, the cross-section of the head is configured as a lobular shape, similar to that of a cam, having a constant radii along one hemisphere of the head, and smaller radii along the opposing hemisphere of the head, with the smallest radius existing approximately perpendicular to the midline of the head member.

These and other objects, features and advantages of the present invention, will become more apparent to those skilled in the art from the following more detailed description of the preferred embodiments of the invention, taken with the accompanying figure drawings.

DETAILED DESCRIPTION OF THE PREFERRED EMBODIMENTS

Figure 1:
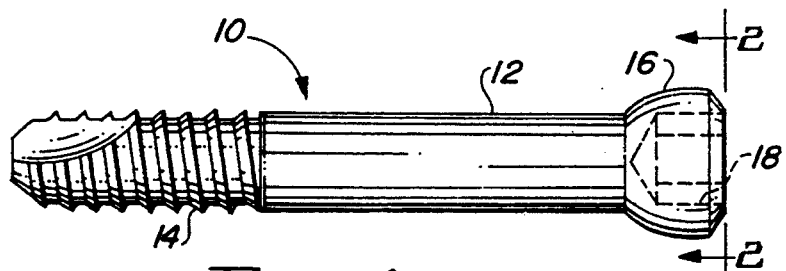
FIG. 1 is a side elevational view of a bone screw of the prior art.
Figure 2:
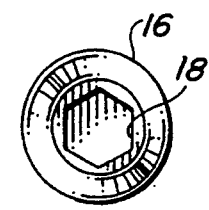
FIG. 2 is an end elevational view taken along line 2—2 of FIG. 1, illustrating the head configuration of the prior art bone screw.

FIGS. 1 and 2 illustrate bone screws as are known in the art, and as are typically employed in reducing fractures, particularly of the skeletal structure of the hands and feet. Those skilled in the art will understand and recognize, however, that the inventive bone screw has utility and application to reducing fractures of virtually any bone capable of receiving a pilot hole and being coupled with a bone screw. Reference to the specific bones of the hands or feet, particularly to the metacarpal or metatarsal bones, is merely for purposes of illustration and reference, and is not intended to be, nor should those in the art construe such reference to be, limiting to the scope and application of the inventive bone screw.

The prior art bone screw 10, illustrated in FIGS. 1 and 2, is characterized as a lag screw having a self-tapping threaded end portion 14 and an un-threaded smooth shaft portion 12. A head member 16 has an associated hexagonal recess 18 for engaging a suitable tool used to drive the screw into the bone tissue. The bone screw 10 may be cannulated (not shown) to permit insertion of a guide wire. The head member 16 is generally circular in cross-sectional shape, and has uniform radii about its entire circumference. When the conventional bone screw 10 is used to reduce a fracture of the metatarsal bone, the head member 16 typically protrudes above the bone surface and impinges upon the adjacent muscle and ligaments, causing irritation and inflammation of the adjacent tissue.

The inventive bone screw 20, illustrated with reference to FIGS. 3–5, may be a lag screw consisting of a threaded end (not shown), which may be self-tapping or not, and a non-threaded shaft, or may be a non-lag screw having threads along the entire length of the shaft 22. Like the prior art bone screw 10, the inventive bone screw 20 may also be cannulated to accommodate a guide wire. The inventive bone screw 20, however, has a head member 24, which has a lobular cross-sectional shape characterized by a tapered hemispherical portion 26. The head member 24 has first cross-sectional hemisphere having uniform or constant radii, while the opposing tapered hemispherical portion 26 has smaller radii relative to the first hemispherical portion, with the smallest radius existing approximately perpendicular to the midline 28 of the head member 24.

Figure 3:
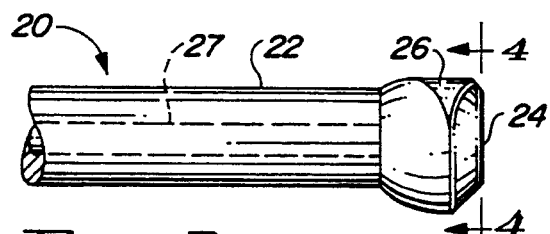
FIG. 3 is a fragmentary side elevational view of the inventive bone screw.
Figure 4:
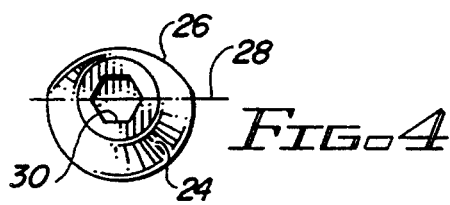
FIG. 4 is an end elevational view taken along line 4—4 of FIG. 3, illustrating the head configuration of the inventive bone screw.

As illustrated in FIGS. 3 and 4, the tapered hemispherical portion 26 resides on a lateral aspect of the head member 24. The tapered hemispherical portion 26 presents a smaller surface area on one lateral surface of head member 24 relative to the other first hemisphere of the head member 24. This head member 24 configuration facilitates locating the bone screw in a position which presents the tapered hemispherical portion 26 in a co-planar, substantially co-planar or closely proximate position relative to the surface of the bone. In this manner, the head portion 24 of the inventive bone screw 20 minimizes the surface area protruding from the bone which is exposed to and impinges upon adjacent soft tissue.

Figure 5:
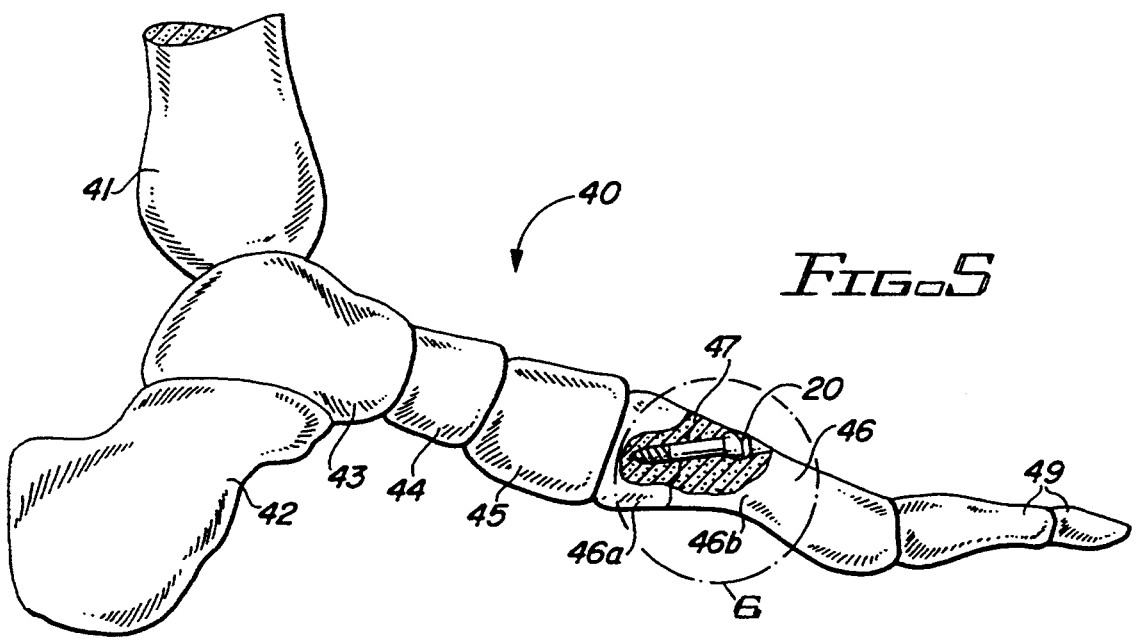
FIG. 5 is an internal view of the bones of the left foot illustrating reduction of a fracture of the 1st metatarsal with the inventive bone screw.
Figure 6:
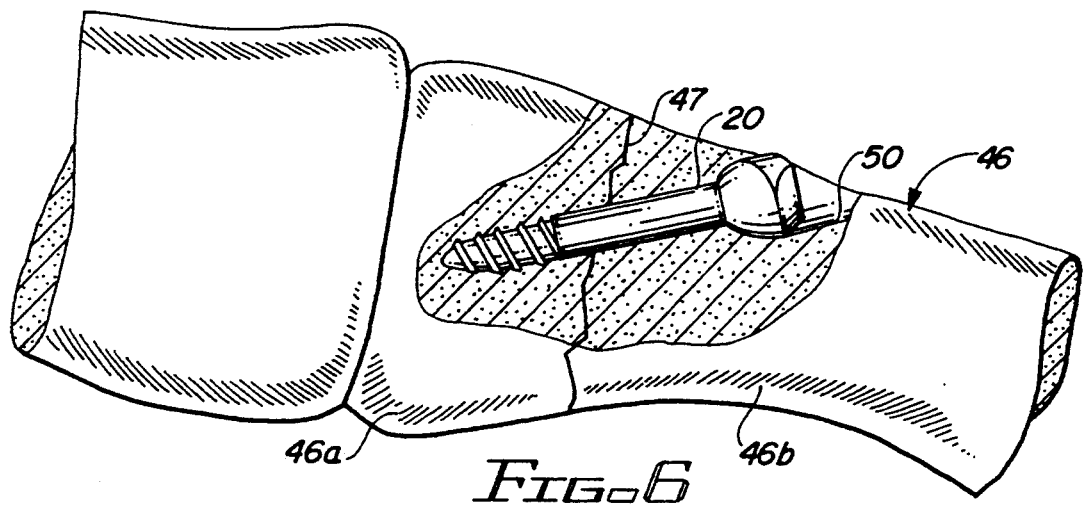
FIG. 6 is a fragmentary view taken from circle 6 of FIG. 5, illustrating the fracture reduced with the inventive bone screw.

FIGS. 5 and 6 illustrate a reduced metatarsal fracture using the inventive bone screw 20. In FIG. 5 there is shown an inner view of the left foot 40 representing the skeletal structure of the foot. The relevant skeletal features include the tibia 41, os calcis 42, astragalus 43, navicular 44, internal cuneiform 45, metatarsus 46 and phalanges 47 of the great toe. A fracture 47 of the base of the 1st metatarsal bone 46 separates the metatarsus into two pieces 46a and 46b. The inventive bone screw 20 is used to compress metatarsal pieces 46a and 46b into proper physiological alignment, thereby reducing the fracture 47. As illustrated in FIG. 6, the head member 24 of the inventive bone screw 20 presents very little surface area above the bone surface. Moreover, the inventive bone screw may be counter-sunk into a pre-drilled guide hole 50 to further minimize the protruding surface area.

In practice, the physician reduces a fracture by joining the fractured bone pieces 46a and 46b, drilling a guide hole 50 through the pieces 46a and 46b, inserting the bone screw 20 into the guide hole 50 and compressing the pieces 46a and 46b using an appropriate tool to drive the bone screw 20 into the pre-drilled guide hole 50. Because the screw 20 is provided with the asymmetrical head portion 24, the final step is to adjust the head portion by rotating the bone screw 20 so that the tapered hemispherical portion 26 is presented in alignment with the surface of the bone, thereby minimizing protrusion of the screw 20 into the adjacent soft tissue.

The inventive bone screw 20 may be made of any material suitable and accepted for medical use for the intended purpose. Specifically, surgical steel or other metals, or biocompatible materials, such as plastics, may be used.

While the invention has been described with reference to the preferred embodiments thereof, those skilled in the art will understand and appreciate that variations in materials selection, size, dimension, or configuration are contemplated as falling within the spirit and scope of the description.

What is claimed is:

1. A bone screw, comprising a shaft portion and a head portion, said shaft portion being threaded on at least a section thereof, and said head portion having a first portion with a circular cross-section taken perpendicular to a longitudinal axis of said head portion and a second portion having a generally ellipsoidal cross-section, taken perpendicular to a longitudinal axis of said head portion, said second portion being generally outwardly convex about its perimeter relative to a central axis of said bone screw, wherein said first portion begins and ends in continuation with said second portion.

2. The bone screw of claim 1, wherein said head portion further comprises a generally lobular cross-sectional shape.

3. The bone screw of claim 1, wherein said head portion further comprises a generally cam-shaped cross-sectional shape.

4. The bone screw of claim 1, wherein said circular cross-section of said first portion further comprises substantially uniform radii relative to said central axis of said bone screw and said generally ellipsoidal cross-section of said second portion further comprises smaller radii relative to said central axis than said radii of said circular cross section.

5. The bone screw of claim 4, wherein said hemielliptical cross-sectional portion further comprisses gradually smaller radii relative to said central axix of said bone screw, wherein a smallest radius is present at a point on the circumference of the head portion corresponding to a smallest diameter of said head portion.

6. The bone screw of claim 1, further comprising a longitudinal cannula extending an entire longitudinal aspect of said bone screw.

7. A device for reducing fractures, comprising a screw having a threaded surface formed on at least an end of said screw adapted in use to engage bone tissue; said screw further comprising a head having an asymmetrical lobular cross-sectional shape taken perpendicular to a longitudinal axis of said head and defining a generally ellipsoidal side aspect and a generally circular side aspect of said head, said ellipsoidal side aspect being generally outwardly convex about its perimeter and forming a truncation of the circular shape of said circular side aspect, beginning and ending in continuation with said generally circular side aspect, and having a regular ellipsoidal surface substantially without protuberances and depressions therein and means for engaging a tool for driving said screw into bone tissue.

8. The device for reducing fractures according to claim 7, wherein said circular side aspect comprises substantially uniform radii relative to a central axis of said bone screw and said elliposdal side aspect comprises smaller radii relative to said central axis than said radii of said circular side aspect.

9. The device for reducing fractures according to claim 7, further comprising a longitudinal cannula extending an entire longitudinal aspect of said bone screw.

10. A method for reducing a fracture, comprising the steps of:
   A. joining the fractured bones in physiologically correct alignment;
   B. drilling a guide hole through the fractured bones at an angle of incidence sufficient to anchor and compress a fixation device in the fractured bones;
   C. inserting a fixation device into said drilled guide hole, said fixation device comprising a head having an ellipsoidal side portion with an ellipsoidal cross-section perpendicular to a longitudinal axis of said fixation device, wherein said head of said fixation device is substantially co-planar with the surface of the bone being reduced; and
   D. compressing the fracture by torquing said fixation device, counter-sinking said fixation device in said guide hole and orienting said ellipsoidal side portion substantially coplanar with the surface of the bone being reduced.

11. The method according to claim 10 wherein said step of inserting a fixation device further comprises the step of selecting a fixation device having a head comprising a first circular cross-sectional portion taken a long a longitudinal axis of the fixation device having substantially uniform radii relative to a central axis of said bone screw and a second ellipsoidal cross-sectional portion having smaller radii relative to said central axis than said radii of said first circular cross-sectional portion.

12. The method according to claim 11, wherein said step of inserting a fixation device further comprises the step of selecting said fixation device such that said second hemielliptical cross-sectional portion further comprises gradually smaller radii relative to said central axis of said bone screw, wherein a smallest radius is present at a point on the circumference of the head portion corresponding to a smallest diamter of said head portion.

13. A method for reducing a fracture, comprising the steps of:
   A. joining the fractured bones in physiologically correct alignment;
   B. drilling a guide hole through the fractured bones at an angle of incidence sufficient to anchor and compress a fixation device in the fractured bones; and
   C. inserting and compressing a fixation device, said fixation device comprising a head having a side portion thereof, said side portion having a generally ellipsoidal cross-section taken perpendicular to a longitudinal axis of said fixation device and without substantial protuberances and depressions, said generally ellipsoidal side portion being outwardly convex about its perimeter relative to a central axis of said fixation devices, such that when the fixation device is counter-sunk in the guide hole and said head of said fixation device is at an acute angel relative to the longitudinal axis of the bone, said ellipsoidal side portion of said head is substantially co-planar with and does not project substantially from the surface of the bone being reduced.

14. The device for reducing fractures according to claim 8, wherein said ellipsoidal side aspect further comprises gradually smaller radii relative to said central axis of said bone screw, wherein a smallest radius is present at a point on a circumference of the head portion corresponding to a smallest diameter of said head portion.

* * * * *